United States Patent [19]
Hanamoto et al.

[11] 4,409,335
[45] * Oct. 11, 1983

[54] METHOD FOR ELIMINATING GLUCOSE DEPENDENT SCHIFF BASE EFFECT FROM HEMOGLOBIN A₁ ASSAY

[75] Inventors: Mark S. Hanamoto, Mill Valley; Steve K. Tanaka, Vallejo, both of Calif.

[73] Assignee: Bio-Rad Laboratories, Inc., Richmond, Calif.

[*] Notice: The portion of the term of this patent subsequent to Jun. 21, 2000 has been disclaimed.

[21] Appl. No.: 382,899

[22] Filed: May 28, 1982

[51] Int. Cl.³ .................. G01N 33/66; G01N 33/72
[52] U.S. Cl. .................................. 436/67; 210/656; 422/61; 436/95
[58] Field of Search ............... 436/67, 95; 422/61; 210/656

[56] References Cited
U.S. PATENT DOCUMENTS

| | | |
|---|---|---|
| 4,142,855 | 3/1978 | Acuff. |
| 4,142,856 | 3/1978 | Acuff. |
| 4,142,857 | 3/1978 | Acuff. |
| 4,142,858 | 3/1978 | Acuff. |
| 4,168,147 | 9/1979 | Acuff. |
| 4,238,196 | 12/1980 | Acuff. |
| 4,243,534 | 1/1981 | Bulbenko ............... 436/67 X |
| 4,269,605 | 5/1981 | Dean ..................... 436/67 |

OTHER PUBLICATIONS

Bunn et al., "Chromatographic Analysis of Glycosylated Hemoglobin", *Advances in Hemoglobin Analysis*, pp. 83-94, Alan R. Liss, Inc., NY (1981).
Bunn et al., *Science*, 200, pp. 21-27 (1978).
Chou et al., *Clin. Chem.*, 24(10), pp. 1708-1710 (1978).
F. Maquart et al., *Clinica Chimica Acta*, 108(2), 329-332 (1980).
Goldstein et al., *Diabetes*, 29, pp. 623-628 (1980).
Svendsen et al., *Diabetologia*, 19, pp. 130-136 (1980).
Widness et al., *J. Lab. Clin. Med.*, 95(3), pp. 386-394 (1980).

*Primary Examiner*—Sidney Marantz
*Attorney, Agent, or Firm*—Townsend and Townsend

[57] ABSTRACT

An ion exchange method for the separation of hemoglobin A₁ from its Schiff base precursors and from nonglycosylated hemoglobin in a sample of human blood. The known method of lysing the sample, using it to impregnate a weak cation exchange resin, eluting out the glycosylated components with a buffer solution containing from about 0.6 M to about 0.11 M alkali metal ion dissolved therein, and recovering the eluate, is modified by the inclusion of a dihydroxyboryl compound in either the hemolysate, the elution buffer, or both.

16 Claims, No Drawings

METHOD FOR ELIMINATING GLUCOSE DEPENDENT SCHIFF BASE EFFECT FROM HEMOGLOBIN $A_1$ ASSAY

BACKGROUND OF THE INVENTION

1. Field of the Invention

This invention relates to the monitoring and screening of long-term blood glucose levels in patients afflicted with diabetes mellitus. In particular, this invention relates to a method of isolating fast hemoglobins from their glucose dependent Schiff base precursors and other hemoglobin components present in human blood.

It has been known for some time that the quantity of hemoglobin $A_1$ ($HbA_1$), a glycosylated form of adult hemoglobin (HbA), is higher in the blood of diabetic persons than in that of normal persons. Hemoglobin $A_1$ itself consists of several components, of which the main ones have been identified as $HbA_{1a}$, $HbA_{1b}$ and $HbA_{1c}$. These three components are collectively known as the "fast hemoglobins," since they elute through a chromatographic column relatively quickly. The precursors to these components are labile adducts in which the linkage between the glucose molecule and the hemoglobin molecule in an aldimine linkage (hereinafter referred to as a "Schiff base"). Due to the high reaction rate involved in its formation from glucose and hemoglobin A as well as its high tendency to dissociate back to these starting materials, the Schiff base level reflects short-term fluctuations in the blood glucose levels, rather than the long-term levels sought to be determined in a meaningful diabetic analysis. For this reason, analyses without Schiff base removal are often poor indications of a patient's ability to regulate glucose.

It is therefore desirable to find a method for determining the hemoglobin $A_1$ content of human blood without interference from Schiff base precursors.

2. Description of the Prior Art

A general discussion of glycosylated hemoglobins and their relevance to diabetes mellitus is offered by Bunn, et al., *Science,* 200, pp. 21-27 (1978). The use of ion exchange resins is described by Chou, et al., *Clin. Chem.,* 24(10), pp. 1708-1710 (1978) and in a series of U.S. patents to Acuff: Nos. 4,142,855, 4,142,856, 4,142,857 and 4,142,858 (all issued on Mar. 6, 1978), 4,168,147 (issued on Sept. 18, 1979) and 4,238,196 (issued on Dec. 9, 1980).

Known methods for removing Schiff base adducts include saline incubation of erythrocytes and dialysis of the hemolysate. The former is described by Goldstein, et al., *Diabetes,* 29, pp. 623-628 (1980), Svendsen, et al., *Diabetologia,* 19, pp. 130-136 (1980) and Chou, et al., *Clin. Chem.,* 24(10), pp. 1708-1710 (1978). The latter is described by Goldstein, et al., supra, and Widness, et al., *J. Lab. Clin. Med.,* 95(3), pp. 386-394 (1980).

Accurate analysis for $HbA_{1c}$ without prior removal of Schiff base has been achieved by a colorimetric technique using acid hydrolysis followed by treatment with thiobarbituric acid. This is described in Svendsen, et al., supra.

The use of borate ion in conjunction with an anion exchanger is disclosed in Bunn, et al., *Advances in Hemoglobin Analysis,* pp. 83-94, Alan R. Liss, Inc., N.Y. (1981), to retard the elution of glycosylated moieties in a sample where no Schiff base is present.

SUMMARY OF THE INVENTION

A method is provided for the separation of hemoglobin $A_1$ from its Schiff base precursors in a sample of human blood which avoids the need for saline washes, hemolysate dialysis or complicated analytical techniques. The method involves an improvement in the known cation exchange method of lysing the sample, impregnating a cation exchanger with the hemolysate and eluting out the desired components with a buffer solution. The improvement comprises the inclusion of a dihydroxyboryl compound in either the hemolysate, the elution buffer, or both.

DESCRIPTION OF THE PREFERRED EMBODIMENTS

The present invention resides in the enhanced dissociation of Schiff base precursors in the known cation exchange method for hemoglobin $A_1$ analysis. The enhanced dissociation is achieved by the inclusion of a dihydroxyboryl compound in either the hemolysate, the elution buffer, or both.

Preferred dihydroxyboryl compounds are boric acid, lower alkyl boronic acids, preferably $C_1$-$C_3$ alkylboronic acids and salts thereof. Examples of alkylboronic acids are methylboronic acid, ethylboronic acid, propylboronic acid, 3-methyl-1-butylboronic acid, etc. Boric Acid and other forms of borate ion are particularly preferred. Preferred salts are alkali metal salts.

For inclusion in the hemolysate, the compound can be added before or after hemolysis, depending on the hemolysis technique used. Hemolysis can be applied either to the entire blood sample or to any measured portion thereof. While the red blood cells can be separated from the bulk of the sample by centrifugation, such separation can be omitted with no detriment to the analysis itself. Thus, it is most convenient to apply the hemolysis technique to the entire sample. Any technique which will rupture the membranes of the red blood cells sufficiently to release the cell contents to the surrounding fluid will suffice. This includes any conventional hemolysis technique. Examples are agitation, the use or organic hydrophobic solvents, osmotic shock and the use of aqueous detergents. The use of aqueous detergents is preferred. Examples of suitable detergents are polyoxyethylene ethers of higher aliphatic alcohols, alkylaryl polyether alcohols, sulfonates and sufates and polyoxyethylene derivatives of fatty acid esters of sorbitol anhydrides. Many such detergents are commercially available, including "Brij" ® (ICI United States, Inc., Wilmington, Del.), "Triton" ® (Rohm and Haas Co., Philadelphia, Pa.) and "Tween" ® (Atlas Chemical Industries, Inc., Wilmington, Del.). The amount of detergent used for hemolysis is not critical and may be any amount sufficient to cause lysis to occur in a reasonable amount of time without affecting the retention characteristics of the cation exchanger when the detergent passes therethrough as part of the hemolysate. A convenient range is from about 0.1 to about 0.5 weight percent detergent based on the sample plus aqueous solution.

When a detergent is used for the hemolysis, the dihydroxyboryl compound may be added to the aqueous detergent prior to contact of the detergent with the blood sample. The amount of dihydroxyboryl compound is not critical and any effective amount can be used, i.e., any amount which will cause dissociation of the Schiff base and not produce a substantial salting out effect in the ion exchanger. The preferred concentration of dihydroxyboryl compound in the hemolysate is from about 0.1 M to about 1.0 M, most preferably from about 0.4 M to about 0.6 M. It is further preferred, once the dihydroxyboryl compound has been added, to adjust the pH of the hemolysate to within about 4.5 to about 6.5, more preferably about 5.0 to about 6.0, by adding base. In typical practice, the detergent solution containing the dihydroxyboryl compound is combined with the blood sample and the resulting mixture is incubated at room temperature for at least about ten minutes.

When a dihydroxyboryl compound is included in the elution buffer, the amount is again not critical and any effective amount can be used, i.e., any amount which will cause Schiff base dissociation without producing a substantial salting out effect in the ion exchanger. The preferred concentration in the elution buffer is from about 0.01 M to about 0.15 M, most preferably from about 0.07 M to about 0.10 M.

It is preferred that the dihydroxyboryl compound be included in the hemolysate, and it is particularly preferred that the dihydroxyboryl compound be included in both the hemolysate and the elution buffer.

Although the remaining features of the analysis are known, the following discussion is offered to provide further clarification.

Any conventional cation exchange resin with a weakly acidic character can be used. Examples of suitable resin matrices are acrylic, methacrylic and phenolic polymers, as well as polystyrene, polyvinyl compounds, cellulose, and agarose. Examples of active groups of a weakly acidic character are carboxylic, methylcarboxylic and phosphoric acid groups. A preferred resin is a copolymer of methacrylic acid and divinylbenzene. The particle size of the resin is not critical and will vary with the type of column used. It will be most convenient to use particles of a size between 100 and 400 mesh (U.S. Sieve Series), preferably between 200 and 400 mesh.

When a copolymer of methacrylic acid and divinylbenzene is used, it is preferred that about 30% to about 50%, more preferably about 35% to about 45%, of the active sites on the resin are coupled by ions of an alkali metal, the remainder being occupied by hydrogen ions. The term "alkali metal" is intended to designate the metals of Group 1-A of the periodic table. Preferred metals are those with an atomic weight equal to or less than that of potassium. Of these, sodium and potassium are particularly preferred, and sodium is the most preferred. Adjustment of the ionic ratio is conveniently achieved by the use of an acidic buffer solution, e.g., phosphoric acid, and must be completed prior to impregnation.

Although any conventional configuration can be used for the cation exchange resin, the resin is preferably arranged in a vertical column as a fixed bed. Any conventional means of impregnating the column with the hemolysate can be used. In a gravitational flow column, impregnation is conveniently achieved by applying the hemolysate by syringe or pipette to the top of the resin bed and allowing it to disperse by gravity through the particle interstices into the bulk of the bed.

The volume of hemolysate is not critical, and is typically several orders of magnitude smaller than the volume of the cation exchange resin bed. This will insure full interaction between the hemolysate and the resin particles and provide ample opportunity for ion exchange and component separation during the elution. Typically, the hemolysate will permeate only the entry region on the bed, leaving the remainder for further interaction during the elution.

Following impregnation of the resin with the hemolysate, the elution buffer is passed through the resin. In addition to the considerations mentioned above (i.e., regarding the amount of dihydroxyboryl compound present), the composition and volume of the buffer are adjusted to result in the collection of all the $HbA_{1a}$ and $HbA_{1b}$ and substantially all of the $HbA_{1c}$, with dissociation of the Schiff base precursors to glucose and nonglycosylated hemoglobin. Higher elution volumes will provide more complete Schiff base dissociation.

The elution buffer contains alkali metal ions at a concentration appropriate to achieve the desired separation. The appropriate concentration depends on the particular alkali metal used, but will generally lie within the range of about 0.06 M to about 0.11 M, preferably about 0.07 M to about 0.09 M. As on the resin itself, alkali metals with an atomic weight equal to or less than that of potassium are preferred, with sodium and potassium particularly preferred and sodium the most preferred.

The pH of the buffer is not critical and is subject only to the need to avoid hydrolysis of the hemoglobins by excess acidity and to effect the desired separation. In general, the pH will fall within the range of about 5.0 to about 7.5, preferably from about 6.5 to about 7.0. Any conventional buffer system with a pH within this range can be used. Examples include biochemical buffers, zwitterionics and phosphate buffers. Preferred buffers are potassium and sodium phosphates, both monobasic and dibasic. Sodium phosphates are particularly preferred.

The temperature considerations of the process are similar to those of any ion exchange process. The appropriate temperature will thus depend on the volume of resin in the column, the particle size and alkali metal content of the resin, the particle surface area and other similar variables, and can readily be determined by routine experimentation. It will be most convenient to operate at a temperature within the range of about 14° C. to about 35° C., preferably from about 19° C. to about 30° C.

The volume of elution buffer and its flow rate through the cation exchange resin will be selected to provide the optimum separation. The optimum volume and flow rate are readily determined by routine experimentation.

Conventional stabilizers, for example sodium azide and/or ethylenediamine tetraacetic acid, can be included in the elution buffer in convenient amounts.

In general, the dissociation of Schiff base adducts may be enhanced by elongation of the elution time. This is accomplished in any conventional way, including the following, either alone or in combination: lowering the percentage of active sites on the resin which are occupied by alkali metal ions; lowering the alkali metal concentration in the elution buffer; raising the volumetric quantity of resin in proportion to the sample volume; decreasing the resin particle size, imposing flow restrictions on the exchanger, etc.

Once the elution is complete, the resulting eluate will contain substantially all of the hemoglobin $A_1$ present in the original sample and substantially none of the nonglycosylated hemoglobin. The eluate can then be analyzed for its $A_1$ content by any conventional technique, including biochemical techniques and spectrophotometric techniques well known in the art.

The following example is offered to further illustrate the invention and is intended to neither limit nor define the invention in any manner.

EXAMPLE 1

This example demonstrates the use of the process of the present invention in analyzing Schiff-base-containing samples of human blood for their non-Schiff base glycosylated hemoglobin content.

Whole blood samples from four nondiabetic persons were split into two portions apiece. One portion from each pair was incubated with 900 mg/dl of glucose for five hours at 37° C., to be used as samples containing Schiff base. The remaining portions were stored at 4° C. until assay time, whereupon they were used as samples without Schiff base (the actual amount of Schiff base in these samples was negligible, since they were stored for eighteen days before use).

Aliquots of both the incubated and unincubated samples were then lysed and separated in ion exchange columns in the manner described below.

A. Hemolysis

A well-mixed 100 μl aliquot of each sample was combined with 500 μl of a hemolysis reagent consisting of a 0.33% (by volume) aqueous solution of a polyoxyethylene ether surfactant bearing the trade name "Triton X-100"® (Rohm and Haas Co., Philadelphia, Pa.) and boric acid at a concentration of 0.6 M. The mixture was vortexed and allowed to stand for five minutes. A 200 μl aliquot of each resulting hemolysate was then set aside for comparison with the eluted samples obtained in the following steps.

B. Elutions

A series of ion exchange resin columns were prepared as follows: Bio-Rex 70 ion exchange resin, a weakly acidic resin consisting of a copolymer of methacrylic acid and divinylbenzene, obtainable from Bio-Rad Laboratories, Richmond, Calif., was conditioned with phosphoric acid to achieve a 55:45 ratio of hydrogen ions to sodium ions at the active sites of the resin. A plastic resin column, approximately 12 cm in length with a volumetric capacity of approximately 12 ml and containing a frit near the bottom, was charged with 1.0 g (3.0 ml) of the preconditioned resin. The column was shaken to provide a uniform suspension. Immediately after shaking, the cap at the top of the column was removed and the tip at the bottom was snapped off to permit the column to drain into a waste container.

Once the column was drained, a 100 μl aliquot of hemolysate was transferred by pipette onto the center of the top of the resin bed. The bed was then allowed to stand for 5–7 minutes.

An elution buffer solution was then passed through the column. The solution contained 0.05 M phosphate buffer with a pH of 6.7 and a sodium ion concentration of 74 meq/L. A total of 10.0 ml of the solution was used, the first ml of which was added dropwise to the top of the column and the remainder directed in a stream against the column wall.

After the column had completed drained, the eluate was mixed thoroughly and transferred to a cuvette with a 10 mm light path and its absorbance read on a laboratory spectrophotometer at 415 nm which had been zeroed with the buffer solution as a blank.

To express the hemoglobin content in the eluate as a percentage of the total hemoglobin present in the original sample, a similar absorbance measurement was taken on the hemolysate aliquot which had been set aside (see: last sentence under "Hemolysis" section, above) after dilution with the second elution buffer. The percent in the eluate was then determined by the following formula:

$$\text{Percent hemoglobin in eluate} = \frac{\text{Absorbance of eluate}}{5 \times (\text{Absorbance of hemolysate})} \times 100$$

This represents the level of $HbA_1$ as a percentage of the total hemoglobin in the original sample. Both the incubated and unincubated hemolysates were eluted by this procedure.

C. Total Schiff Base Determination

In order to determine the total Schiff base in the hemolysates, the prior art buffer was used with no borate ion present. This consisted of 4.0 ml of a 0.05 M phosphate buffer with a pH of 6.7 and a sodium ion concentration of 74 meq/L. Due to the sodium ion content of this buffer and the sodium:hydrogen ion ratio on the ion exchanger (the same as that used above), all of the fast hemoglobins plus Schiff base adducts collected in the eluate. The amount of HbA in the eluate, as a percentage of the total hemoglobin in the original sample, was then calculated as in Section B, above.

D. Results

Four different experiments were run on each sample, using varying amounts of borate ion in both the hemolysis reagent and the elution buffer as follows:

TABLE I

| | Borate Ion Content of Reagents | | |
|---|---|---|---|
| | Borate Ion Concentration | | Volume of |
| Experiment | Hemolysis Reagent | Elution Buffer | Elution Buffer |
| A | — | — | 4ml |
| B | — | — | 10ml |
| C | 0.6M (pH 5.00) | — | 10ml |
| D | 0.6M (pH 5.00) | 0.09M | 10ml |

Prior to using each of these reagent combinations, slight adjustments were made in the hydrogen to sodium ion ratio in the exchanger from the initial value of 55:45 to provide the optimum separation of $HbA_1$ fraction from the $HbA_0$ fraction. The adjustments were made by treatment with phosphoric acid and the final ratio of each case lay within the range of 55:45 to 60:40.

Eluates from both the incubated and unincubated samples were analyzed for percent of original hemoglobin as indicated above. The results represented the total of the three fast hemoglobins in each sample plus any Schiff base adducts which had not become dissociated. These values were then inserted into the following formula to calculate the amount of Schiff base removed by the process of the invention, expressed in terms of percent of the total amount originally present in the incubated samples:

$$\text{Percent Schiff Base Removed} = \left[ \frac{\left[\frac{\% \, HBA_1 \, (inc.)^*}{\% \, HBA_1 \, (uninc.)^*}\right] - \left[\frac{\% \, HBA_1 \, (inc.)}{\% \, HBA_1 \, (uninc.)}\right]}{\left[\frac{\% \, HBA_1 \, (inc.)^*}{\% \, HBA_1 \, (uninc.)^*}\right] - 1} \right] \times 100$$

Asterisk denotes 4 ml elution performed without borate ion (see Section C above).
"inc." = incubated; "uninc." = unincubated The results are listed in Table II, where it is evident that the percent Schiff base removal is considerably enhanced with the use of borate.

TABLE II
TEST RESULTS

| Experiment | Patient | Unincubated Samples | Incubated with 900 mg/dl Glucose | % Increase Due to Incubation (Average) | % Schiff Base Removed (Average) |
|---|---|---|---|---|---|
| A | 1 | 7.05 | 11.03 | 56.5% | 0% |
|   | 2 | 6.97 | 10.49 | | |
|   | 3 | 7.69 | 11.76 | | |
|   | 4 | 6.32 | 10.49 | | |
| B | 1 | 6.55 | 9.30 | 42.0% | 25.7% |
|   | 2 | 6.64 | 9.04 | | |
|   | 3 | 7.15 | 9.90 | | |
|   | 4 | 5.79 | 8.77 | | |
| C | 1 | 6.84 | 7.23 | 6.5% | 88% |
|   | 2 | 6.20 | 6.99 | | |
|   | 3 | 7.63 | 7.51 | | |
|   | 4 | 5.82 | 6.38 | | |
| D | 1 | 6.69 | 6.91 | 3.5% | 93.8% |
|   | 2 | 6.26 | 6.66 | | |
|   | 3 | 7.51 | 7.38 | | |
|   | 4 | 5.79 | 6.13 | | |

What is claimed is:

1. In a method for the separation of hemoglobin $A_1$ from nonglycosylated hemoglobins and the Schiff base precursors to hemoglobin $A_1$ in a sample of human blood which comprises:
(a) lysing the red blood cells in said sample to form a hemolysate,
(b) impregnating a weak cation exchange resin with said hemolysate,
(c) passing through said resin a buffer solution with ions of an alkali metal dissolved therein at a concentration of from about 0.06 M to about 0.11 M to dissociate said Schiff base precursors into glucose and hemoglobin A and to preferentially elute said glucose and said hemoglobin $A_1$ over said hemoglobin A said other nonglycosylated hemoglobins, and
(d) recovering the eluate from step (c),
the improvement which comprises including an effective amount of a dihydroxyboryl compound in said hemolysate, said buffer solution, or both.

2. A method according to claim 1 in which said improvement comprises including an effective amount of a dihydroxyboryl compound in said hemolysate or in both said hemolysate and said buffer solution.

3. A method according to claim 1 in which said improvement comprises including dihydroxyboryl compound in both said hemolysate at a concentration of from about 0.1 M to about 1.0 M and said buffer solution at a concentration of from about 0.01 M to about 0.15 M.

4. A method according to claim 1 in which said improvement comprises including a dihydroxyboryl compound in both said hemolysate at a concentration of from about 0.4 M to about 0.6 M and said buffer solution at a concentration of from about 0.07 M to about 0.10 M.

5. A method according to claims 1, 2, 3 or 4 in which said dihydroxyboryl compound is selected from the group consistng of boric acid, lower alkyl boronic acids, and salts thereof.

6. A method according to claims 1, 2, 3 or 4 in which said hydroxyboryl compound is boric acid.

7. A method according to claim 1 in which step (a) is performed by adding said sample to an aqueous detergent solution and incubating the resulting mixture at approximately room temperature for at least about ten minutes.

8. A method according to claim 1 in which step (a) is performed by adding said sample to an aqueous detergent solution to produce a mixture containing from about 0.1 to about 0.5 weight percent detergent and incubating said mixture at approximately room temperature for at least about ten minutes, and said improvement comprises including a dihydroxyboryl compound in said detergent solution or in both said detergent solution and said buffer solution, such that the concentration of dihydroxyboryl compound is from about 0.1 M to about 1.0 M in said hemolysate and from about 0.01 M to about 0.15 M in said buffer solution.

9. A method according to claim 1 in which step (a) is performed by adding said sample to an aqueous detergent solution to produce a mixture containing from about 0.1 to about 0.5 weight percent detergent and incubating said mixture at approximately room temperature for at least about ten minutes, and said improvement comprises including boric acid both in said detergent solution to produce a hemolysate containing from about 0.4 M to about 0.6 M borate ion and in said buffer solution at a concentration of from about 0.07 M to about 0.10 M borate ion.

10. A method according to claim 1 in which said weak cation exchange resin is a copolymer of methacrylic acid and divinylbenzene and from about 30% to about 50% of the active sites on said resin are occupied by alkali metal ions, the remainder occupied by hydrogen ions, said alkali metal ions on said resin and in said buffer solution being identical and selected from the group consisting of sodium and potassium.

11. A method according to claim 1 in which said weak cation exchange resin is a copolymer of methacrylic acid and divinylbenzene and from about 35% to about 45% of the active sites on said resin are occupied by sodium ions, the remainder occupied by hydrogen ions, the concentration of alkali metal ions in said buffer solution is from about 0.07 M to about 0.09 M, and said alkali metal ions are sodium ions.

12. A method according to claim 1 in which said buffer solution is a phosphate buffer solution with pH of about 5.0 to about 7.5, and step (c) is performed at a temperature between about 14° C. and about 35° C.

13. A method according to claim 1 in which said weak cation exchange resin is a copolymer of methacrylic acid and divinylbenzene and from about 35% to about 45% of the active sites on said resin are occupied by sodium ions, said alkali metal ions of step (c) are sodium ions and the concentration of said sodium ions in said buffer solution is from about 0.07 M to about 0.09 M, said buffer solution is a phosphate buffer solution with a pH of about 6.5 to about 7.0, and step (c) is performed at a temperature between about 19° C. and about 30° C.

14. In a method for the separation of hemoglobin $A_1$ from nonglycosylated hemoglobins and the Schiff base precursors to hemoglobin $A_1$ in a sample of human blood which comprises:
(a) combining said sample with an aqueous detergent solution to form a mixture containing from about 0.1 to about 0.5 weight percent detergent, and incubating said mixture at approximately room temperature for at least about ten minutes,
(b) impregnating a cation exchange resin with said hemolysate, said resin consisting essentially of a copolymer of methacrylic acid and divinylbenzene with a particle size of about 100 to about 400 mesh on which about 30% to about 50% of the active sites are occupied by sodium ions, the remainder occupied by hydrogen ions,
(c) passing through said resin a phosphate buffer solution with a pH of about 5.0 to about 7.5 at a temperature of from about 14° C. to about 35° C., said buffer solution containing sodium ions dissolved therein at a concentration of from about 0.06 M to about 0.11 M to dissociate said Schiff base precursors into glucose and hemoglobin A and to preferentially elute said glucose and said hemoglobin $A_1$ over said hemoglobin A and said other nonglycosylated hemoglobins, and
(d) recovering the eluate from step (c),
the improvement which comprises including borate ion in said detergent solution such that the mixture of step (a) contains from about 0.1 M to about 1.0 M borate ion, and including borate ion in said buffer solution at a concentration of from about 0.01 M to about 0.15 M.

15. A kit for use in an assay for determining the hemoglobin $A_1$ content in a sample of human blood without interference from glucose dependent Schiff base precursors to hemoglobin $A_1$, said kit comprising:
(a) a weak cation exchanger,
(b) a hemolysis reagent comprising an aqueous detergent solution containing a dihydroxyboryl compound at a concentration of from about 0.1 M to about 1.0 M, and
(c) a buffer solution with ions of an alkali metal dissolved therein at a concentration of from about 0.06 M to abut 0.11 M.

16. A kit according to claim 15 further comprising a buffer solution containing a dihydroxyboryl compound at a concentration of from about 0.01 M to about 0.15 M.

* * * * *